United States Patent [19]
Maihofer

[11] Patent Number: 5,823,340
[45] Date of Patent: Oct. 20, 1998

[54] STERILIZATION CONTAINER

[75] Inventor: Willi Maihofer, Novaggio, Switzerland

[73] Assignee: Nordpunkt AG, Novaggio, Switzerland

[21] Appl. No.: 704,628

[22] PCT Filed: Feb. 28, 1995

[86] PCT No.: PCT/EP95/00723

§ 371 Date: Sep. 4, 1996

§ 102(e) Date: Sep. 4, 1996

[87] PCT Pub. No.: WO95/23617

PCT Pub. Date: Sep. 8, 1995

[30] Foreign Application Priority Data

Mar. 4, 1994 [DE] Germany ............... 44 07 220.1

[51] Int. Cl.⁶ ............ B65D 83/10; B65D 51/16; B65D 45/32; G05D 16/00
[52] U.S. Cl. ............ 206/370; 206/366; 220/203; 220/319; 220/320; 220/321; 220/686; 422/112; 422/300
[58] Field of Search ............ 220/203, 319, 220/320, 321, 686; 206/366, 370; 422/112, 300

[56] References Cited

U.S. PATENT DOCUMENTS 4,796,776  1/1989  Dalquist et al. ............ 220/203
5,495,941  3/1996  Leonard ............ 206/366

Primary Examiner—Donald E. Adams
Assistant Examiner—Hankyel T. Park
Attorney, Agent, or Firm—Browdy and Neimark

[57] ABSTRACT

The invention concerns a sterilization container which is preferably intended for hospital waste and is formed by a bin (1) having a filler opening, which is delimited by the upper edge of the side wall (5) of the bin and is opposite the base (4) thereof, and a lid (2) for covering the filler opening. The bin (1), and possibly also the lid (2), consists of a tough plastics material which is permeable to microwaves and is still resistant to elongation above the boiling point of water. A pressure-tight sealing arrangement (20), disposed between the bin (1) and the lid (2), and a closure arrangement (3, 29), for securing the lid (2) on the bin (1) against the effect of internal pressure in the bin (1), ensure that the contaminated waste collected in this waste-collection container can be sterilized when the container has been hermetically closed and the waste has been moistened by microwave radiation and then disposed of in the sterile state. Owing to the material from which it is constructed, the container withstands the internal pressure which builds up during this process.

39 Claims, 6 Drawing Sheets

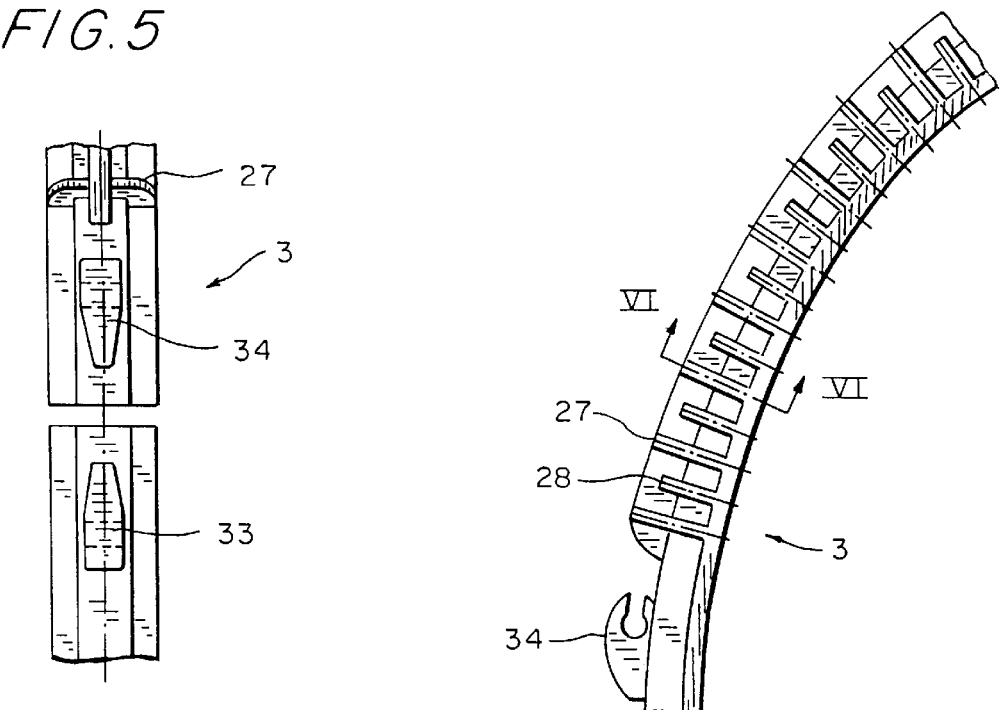
FIG. 5
FIG. 4
FIG. 6

STERILIZATION CONTAINER

TECHNICAL FIELD

The invention relates to a sterilization container, preferably for hospital refuse.

PRIOR ART

A sterilization container of this kind has a receptacle, whose top opening can be closed with a lid, and is primarily designated for hospital refuse, but can also be used in other fields, such as drug manufacturing.

In order to sterilize contaminated refuse, this refuse is usually heated with steam. An adequate quantity of sufficiently heated steam must be introduced into the refuse for the purpose of reliably preventing any part of the refuse from not being heated with the steam intensely enough or long enough to be germ-free in all cases. The introduction of superheated steam also involves the danger that contaminated steam, which has cooled down excessively, or insufficiently heated, contaminated air might possibly escape into the environment.

The use of microwave radiation has also been already proposed for sterilizing refuse. Provided that this refuse is fluid, it can easily be heated by microwaves; however, care must be taken that even those zones in the refuse which are insufficiently acted upon by the radiation due to a nonhomogeneity in it are sufficiently heated by means of heat exchange with adjacent zones.

But if the refuse is either completely or partially dry, microwaves are unsuited for heating the refuse. For this reason, it is useful to moisten the refuse until as a result of the evaporation of the water, a sufficient quantity of steam is produced so that a reliable sterilization of the refuse takes place. Since steam cannot be heated further by microwaves because it is gaseous, in order to achieve a sufficient steam temperature, the refuse must be placed in a pressure vessel in which the evaporation temperature rises due to the increased internal pressure caused by the initial evaporation.

Consequently, the use of microwave radiation for sterilizing refuse requires the employment of pressure-tight receptacles for the refuse. However, since receptacles of this kind are usually very costly, for reasons of economy alone, it does not make sense to also use these containers for collecting the refuse prior to sterilization and for hauling away the sterilized refuse.

The handling of contaminated refuse before sterilization is extremely dangerous and the sterilized refuse, for its part, is an ideal, fertile ground for existing germs so that ideally, the sterilized refuse should be supplied for disposal in a package which prevents it from being reinfected.

DE 38 33 281 C1 has disclosed a pressure-tight refuse container which permits a sterilization of solid hospital refuse by means of microwave radiation. Furthermore, DE 42 25 430 A1 discloses a device for disinfecting or sterilizing trash, in particular hospital garbage that is laden with germs and bacteria. In this case, garbage is put into a container, which can be sealed in an airtight manner by means of a pivoting lid with a sealing ring, is moistened with water, if need be, and then irradiated with microwaves.

DESCRIPTION OF THE INVENTION

The object of the invention, therefore, is to embody a container in such a way that within the framework of the above-described problems, it permits the collection, sterilization, and disposal of contaminated or germ-laden refuse in a particularly simple and economical manner.

According to the invention, in a sterilization container according to claim 1, a pressure-tight sealing device and a closure device are provided between the receptacle and the lid of the container to hold the lid on the receptacle counter to the force of an internal pressure in the receptacle and to prevent an inadvertent opening of the lid. Lid and container are comprised of a plastic which, due to its composition, reliably withstands both pressure load and temperature load during the sterilization process and is permeable by microwaves.

A sterilization container of this kind according to the invention can be produced with an expenditure that is on the same order of magnitude as that of prior, simpler refuse containers for contaminated garbage, but due to its construction, is suited to reliably withstand loads which occur, even during sterilization with microwaves. Then the sterilized refuse can be left in the container without its having to be opened; if a certain vacuum sets in after the sterilization, the sterilization container according to the invention withstands this as well. The closure device prevents the inadvertent opening of the container.

After the container is filled and the closure device is set, since the closure device no longer needs to be released before the sterilized garbage is finally disposed of at its destination, in general, there is no reason to open the container because containers of this kind are not opened in normal hospital operation. However, so that the container is not inadvertently opened, the closure device can be advantageously embodied so that it cannot be opened without particular means, such as a key or the like.

Preferred embodiments of the invention are used for improved storage of both receptacles that are still empty and ones that are closed, and for improved strength of the container, improved sealing of the container, and improved and more reliable handling of the container.

Furthermore, according to a further embodiment of the invention, a device is provided on the outside of the container according to the invention, by means of which device, the closure device itself can be permanently affixed to the receptacle when it is not holding the lid on the receptacle. Consequently, the closure device cannot be lost. However, because of the state or position of the closure device, it is clear that even if a lid is intended to be placed on it, the receptacle should not be locked yet so that more refuse can be put in it.

Advantageously, a region with reduced wall thickness is provided on the container, most suitably in the lid, preferably in the center of it, which region is surrounded by a suitable stiffening, such as an annular bead, which prevents an excessive bulging from occurring as a result of an internal pressure in the container. The wall thickness of this region is slight so that it can be punctured by means of a correspondingly dimensioned injection needle, by means of which water or some other fluid for moistening the refuse can be injected into the container before the microwave treatment.

After the injection, either the injection needle can be left sealing the perforation created by it, after which the needle itself is closed, or it is possible for a sealing stopper to be inserted through the perforation opening, which stopper expands into a mushroom shape on its end disposed inside the container and is consequently pressed so that it seals against the inside of the container by means of the internal pressure in the container. The section of the sealing stopper disposed outside the container can be welded, headed, or otherwise deformed so that when a vacuum occurs in the container, it does not slip into the container.

The sterilization container according to the invention preferably has a circular cross section, but can also assume any other suitable cross section. The main dimensions of the sterilization container according to the invention preferably correspond to those of a small household wastebasket.

The spatial reference terms used below, such as "top", "bottom", "above", "below" etc. relate to the sterilization container according to the invention, which is set upright on an even surface, with its filling opening on top, and is thus disposed in its use position.

SHORT DESCRIPTION OF THE DRAWINGS

The invention is explained in detail below in conjunction with preferred embodiments with reference to the attached schematic drawings.

FIG. 4 shows a partial top view of a closure ring used in FIG. 1;

FIG. 5 shows a view from the direction V in FIG. 4;

FIG. 6 shows a sectional view along line VI—VI in FIG. 4;

THE BEST WAY TO EMBODY THE INVENTION

Figure 1:
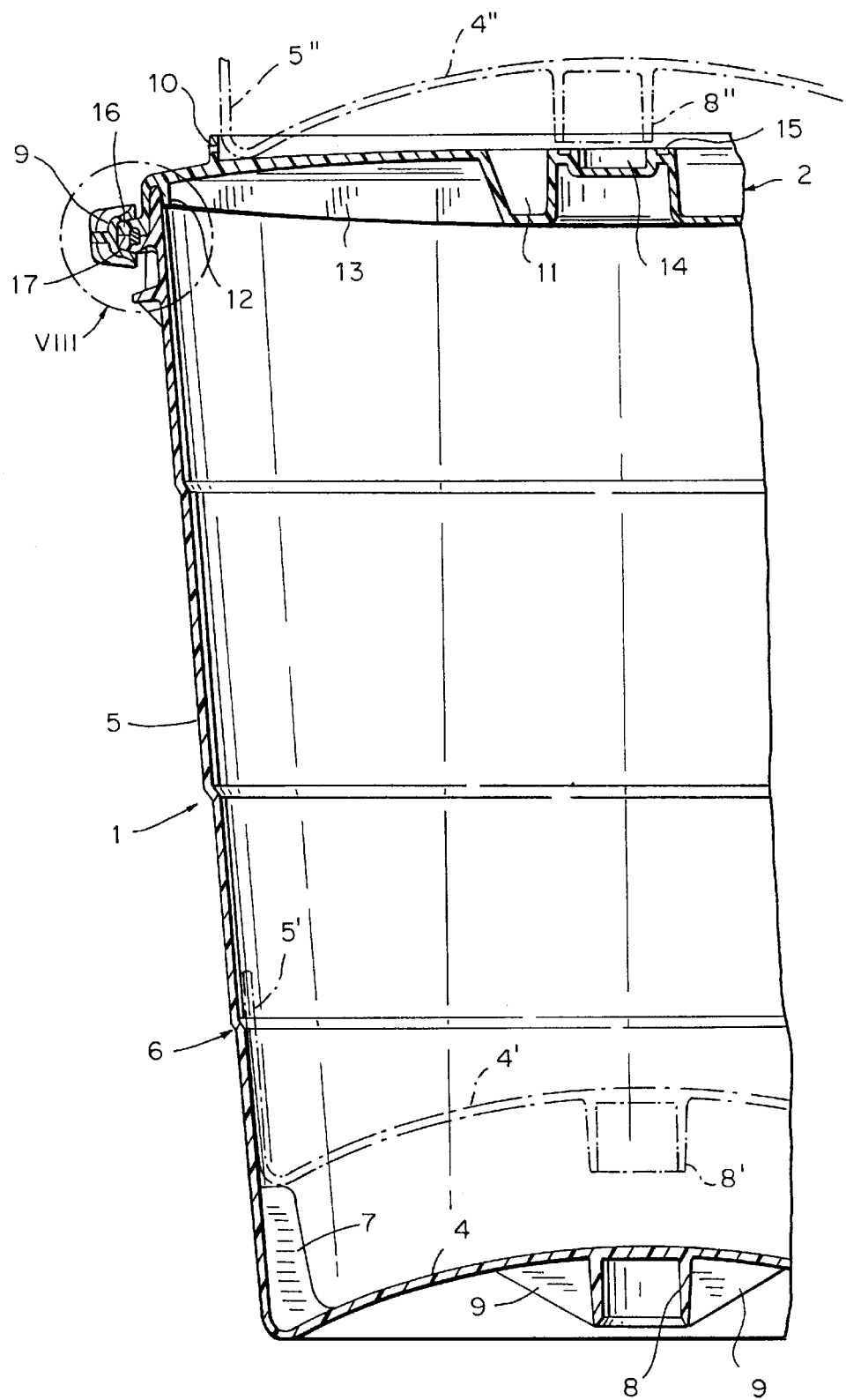
FIG. 1 shows a part of a sectional view of an exemplary embodiment of the container according to the invention, with the lid placed on it.

FIG. 1 shows part of a sectional representation of a receptacle 1 whose side wall 5 is comprised of sections of a truncated cone, which taper toward the bottom and each of which transitions into a smaller section at the bottom, at a step 6 formed there. The receptacle 1 has a bottom 4 that is bowed upward. At the transition between the bottom 4 and the side wall 5, a ring of upright stiffening ribs 7 is embodied on the inside of the receptacle 1, each of which has an upper edge that is essentially flat.

Using dashed lines, FIG. 1 shows the bottom 4' and the side wall 5' of a second receptacle that is stacked for storage inside the receptacle shown. As can be seen, the inner receptacle sits with its bottom circumference edge on the outer circumference of the bottom 4' or with the bottom edge of the side wall 5' on the upper end of all of the bottom-stiffening ribs 7.

In the center of the bottom 4, a tubular fitting 8 extends downward, which is essentially embodied as cylindrical on its jacket face and on its bottom end, is sloped downward from the inside toward the outside. As can be seen in FIG. 1, when the receptacle 1 is not acted upon by an internal pressure, the lower edge of the tubular fitting 8 is disposed above the surface on which the receptacle 1 rests. A ring of fitting-stiffening ribs is embodied between the outside of the tubular fitting 8 and the underside of the bottom 4.

The second receptacle, which is indicated with dashed lines and is inserted into the receptacle 1, also has a tubular fitting 8' that can be seen in the drawing and is spaced considerably apart from the bottom 4 of the first receptacle 1; this spacing is determined by the height of the bottom-stiffening ribs. This height is determined so that all the projections disposed on the outside of the side wall 5, which are described in detail in connection with FIG. 8, rest via the upper edge of the side wall 5 of the receptacle 1 against a second receptacle placed in the receptacle 1 for storage, and in so doing are not damaged and cause no hindrance. Incidentally, the stepped embodiment of the side wall 5 assures that the receptacles inserted into each other for storage sit inside one another without sticking.

The top end of the receptacle 1 is closed by a lid 2, which is bowed upward. Close to the rim of the lid 2, on its top side, an external annular rib 10 is formed, which is embodied as a short cylindrical jacket. The diameter of the external annular rib 10 is dimensioned so that it is slightly larger than the outer circumference of the receptacle 1 on its bottom end.

As shown in the drawing with dashed lines, a second container can be stacked on the lid 2 of the closed container; the bottom end of its side wall 5" and its bottom 4" are shown. In this case, the bottom edge of this upper receptacle sits inside the external annular rib 10, which prevents the upper receptacle from sliding off laterally.

An annular bead 11 that is indented downward is embodied in the center of the lid. An internal annular rib 12 that extends downward is embodied close to the outer circumference of the lid 2; its inner flank is embodied as cylindrical and its outer flank is embodied as a conical jacket that tapers toward the bottom. A group of lid-stiffening ribs 13 are disposed like rays between the inner flank of the internal annular rib 12 and the outer flank of the annular bead 11.

The central region of the lid 2 that is encompassed by the annular bead 11 has an annular groove 15 concentric to the annular bead 11 and the lid 2, which groove is dimensioned so that the bottom edge of the tubular fitting 8" of a receptacle set on top of it for storage can be set down in it if this receptacle is under internal pressure, by means of which the bottom 4" and consequently also the tubular fitting 8" is pressed slightly outward. In the region inside the annular groove 15, a flat recess 14 is embodied whose bottom is embodied as having thinner walls than the other parts of the lid 2 and the receptacle 1.

An outer lid flange 16 is embodied on the underside of the lid 2, which flange rests on an outer receptacle flange 17, which is embodied on the outside of the side wall 5 of the receptacle 1, slightly beneath its upper edge. A closure ring 3 is slid so that it clamps over the two outer flanges 16, 17.

Figure 8:
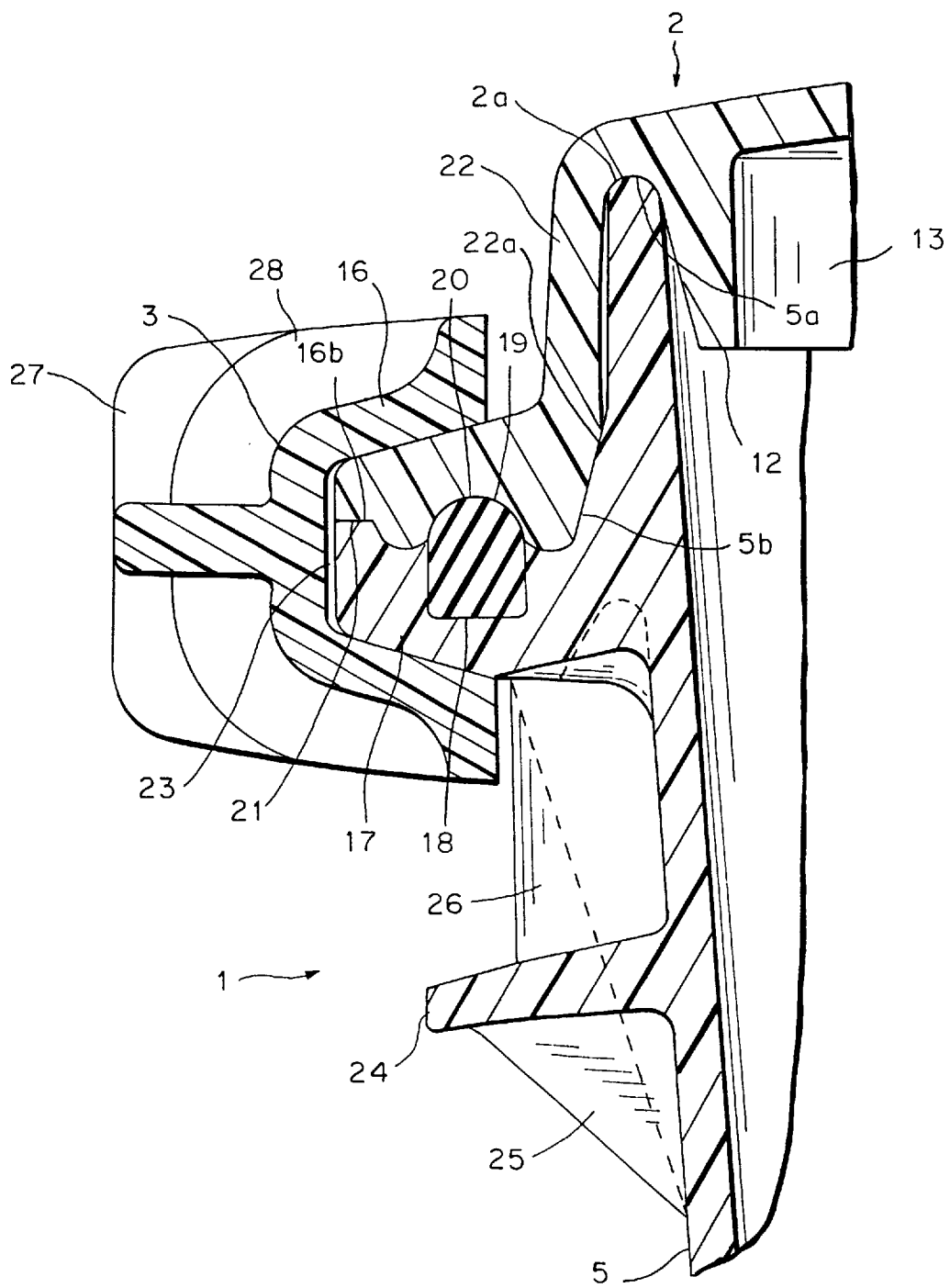
FIG. 8 shows an enlargement of detail VIII in FIG. 1.

FIG. 8 shows an enlargement of detail VIII in FIG. 1 and is explained in conjunction with detail VIII. The elements in FIG. 8 which have already been described in connection with FIG. 1 are not repeated, provided that they are not suited to and required for the explanation.

The outer lid flange 16 and the outer receptacle flange 17 have a flat annular face oriented toward each other; an annular groove 19 with an essentially semicircular cross section is let into the lid side and an annular groove 18 with an approximately square cross section and an equal width is let into the receptacle side.

As can be seen, the side flanks with which the annular groove 19 on the lid side transitions into the bottom surface of the outer lid flange 16 are very rounded. The two annular grooves 18, 19 form an annular channel into which a sealing ring 20 made of flexible material is inserted.

The two rounded parts on both sides of the annular groove 19 on the lid side form narrow pinch zones on both sides of the sealing ring 20, into which the material of the sealing ring 20 can move when it is compressed due to the pressing together of the two outer flanges 16, 17. Consequently, the height of the annular channel formed by the annular grooves 18, 19 is slightly less than the height of the unstressed sealing ring 20, while the cross sectional surface of the annular channel 18, 19 mentioned approximately corresponds to that of the sealing ring 20 or is larger, if need be.

An annular projection 21, which protrudes upward and tapers toward the top and the outside, is embodied on the free outer edge of the outer receptacle flange 17 and is conveniently received in a complementary recess 16b on the outer edge of the outer lid flange 16. The inner edge of the outer receptacle flange 17 transitions with a radius into a conical section 5b of the outer edge of the side wall 5, which section projects further upward and tapers toward the top, and ends in a hollow 5a at the filling opening.

In the bottom section 22a, against which the outer lid flange 16 rests, the outer wall 22 of the lid 2 is embodied as complementary to the bevel 5b of the receptacle side wall 5. Above the complementary section 22a, a sealing groove 2a that opens toward the bottom, whose bottom is rounded and whose side flanks diverge toward the bottom, is embodied between the inner annular rib 12 and the outer wall 22 of the lid 2. As can be seen, the radius of the hollow of the groove bottom of the sealing groove 2a is greater than the radius of the hollow 5a of the upper edge of the side wall 5. In addition, the upper section of the side wall 5 does not touch the flanks of the sealing groove between the outer lid wall 22 and the annular rib 12 in the unstressed state.

The upper surface of the outer lid flange 16 and the lower surface of the outer receptacle flange 17 converge toward the outside; in order to hold these two outer flanges 16, 17 securely together, a closure ring 3 is slid on from the outside, which ring has an inner groove 23 that is embodied so that it is oriented toward the two outer flanges 16, 17 and complementary to their outer faces, and can be clamped onto them. Other details of the closure ring 3 are described further below.

If the ring 3 is slid or pressed onto the two outer flanges 16, 17 from the outside, then a seal is produced:

at the groove bottom of the sealing groove between the outer lid wall 22 and the inner annular rib 12, where the upper edge (hollow 5a) of the side wall 5 rests in a sealed manner, at the complementary conical faces (of sealing regions 22a, 5b) of the outer lid wall 22 and side wall 5, where these two rest against each other with a conical seat, at the horizontal contact surfaces of the two outer flanges 16, 17, between the annular projection 21 and the complementary embodiment (16b) of the outer lid flange 16, and by means of the sealing ring 20.

In this case, the two lateral pinch zones, which adjoin the annular channel that is formed by the annular grooves 18, 19 and contains the sealing ring 20, assure that even when the sealing ring 20 is completely compressed, the two outer flanges 16, 17 rest against each other in a sound and sealed manner.

At a high internal pressure in the receptacle 1, the upper section of the side wall 5, which is disposed inside the sealing ring, is possibly bowed outward. As a result, though, the outer radius of the upper edge of the side wall 5 merely rolls against the groove bottom of the sealing groove. The seal itself is therefore unimpaired.

In order to prevent the outer receptacle flange 17 from deforming or flexing when stressed, this is supported in the direction of the outside of the side wall 5 of the receptacle 1 by means of a ring of stiffening ribs shown in FIG. 8 with a dashed line.

Four brackets 24 are disposed distributed around the outer circumference of the side wall 5 of the receptacle 1, which are embodied in the form of short surface sections that can easily be bent out and down and are supported in the direction of the bottom and the side wall 5 of the receptacle 1 by bracket-stiffening ribs 25. In order to support the outer receptacle flange 17 even better, other stiffening ribs 26 are disposed between its underside and the top side of the brackets 24. The position of the brackets 24 is particularly visible in FIG. 2.

Figure 9:
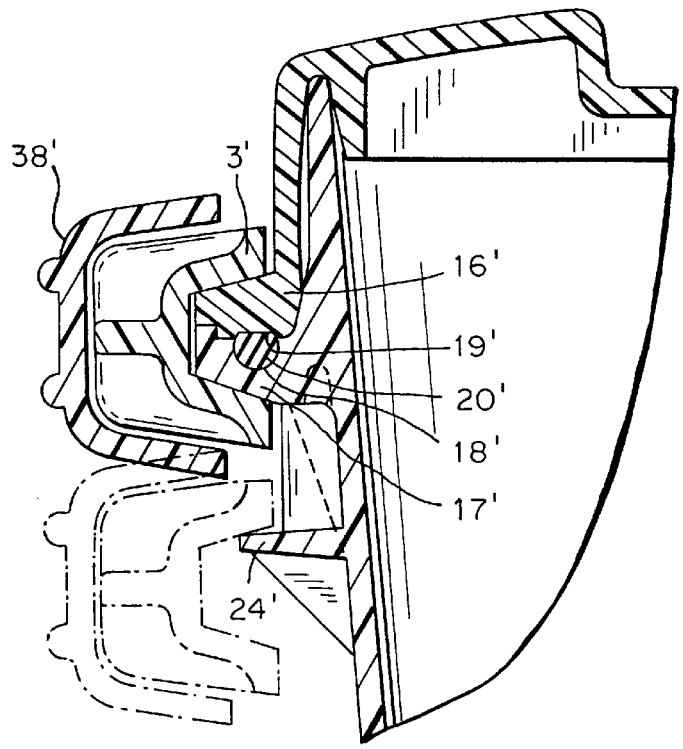
FIG. 9 shows an embodiment similar to FIG. 8.

The closure ring 3, which is disposed in the position shown in FIG. 8 when the container is closed, can be hung on the brackets 24 when the container is empty, as is shown with dot-and-dash lines in FIG. 9. Consequently, when the container is open and the inner chamber of the receptacle 1 is freely accessible, the ring 3 is fastened to the receptacle in captive fashion.

When the container is closed (the ring is disposed in the position in FIG. 8), the brackets 24 are used as handles for lifting the container. This prevents the full, and consequently possibly heavy container from being grasped and lifted by the ring 3, by means of which the seal can be harmed and damage could be caused.

In the version in FIG. 9, as can be seen, the annular groove 18' on the receptacle side is embodied as a groove that is rounded over its entire width; the annular groove 19' on the lid side is embodied as a flat recess with a radius that is very much larger so that the open end of the annular groove 19' on the lid side is much wider than the annular groove 18' on the receptacle side. For this reason, on both sides of the annular seal 20', two very amply sized edge pinch zones are produced into which the seal can move when the lid 3' is clamped on and the deforming that this requires is produced so that the sealing ring 20' does not inhibit the sound reciprocal contact of the two outer flanges 16', 17'.

Figure 2:
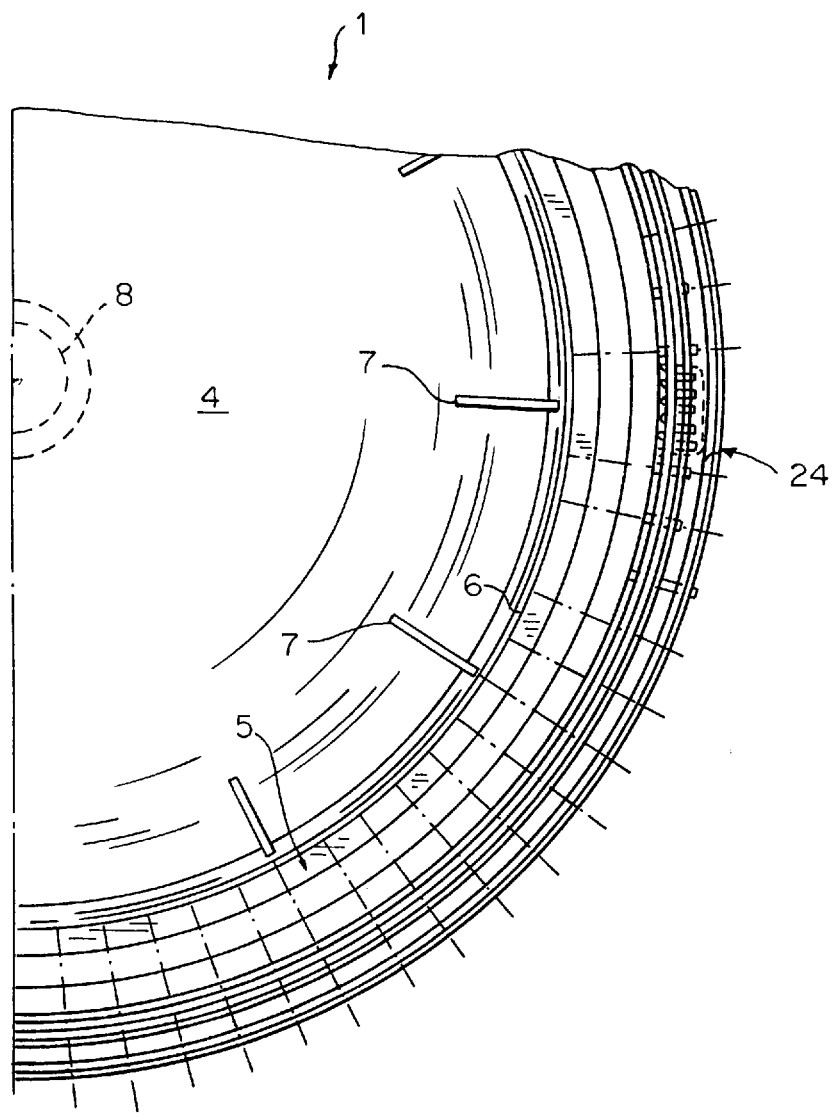
FIG. 2 shows a partial top view of the lid of the container from FIG. 1.
Figure 3:
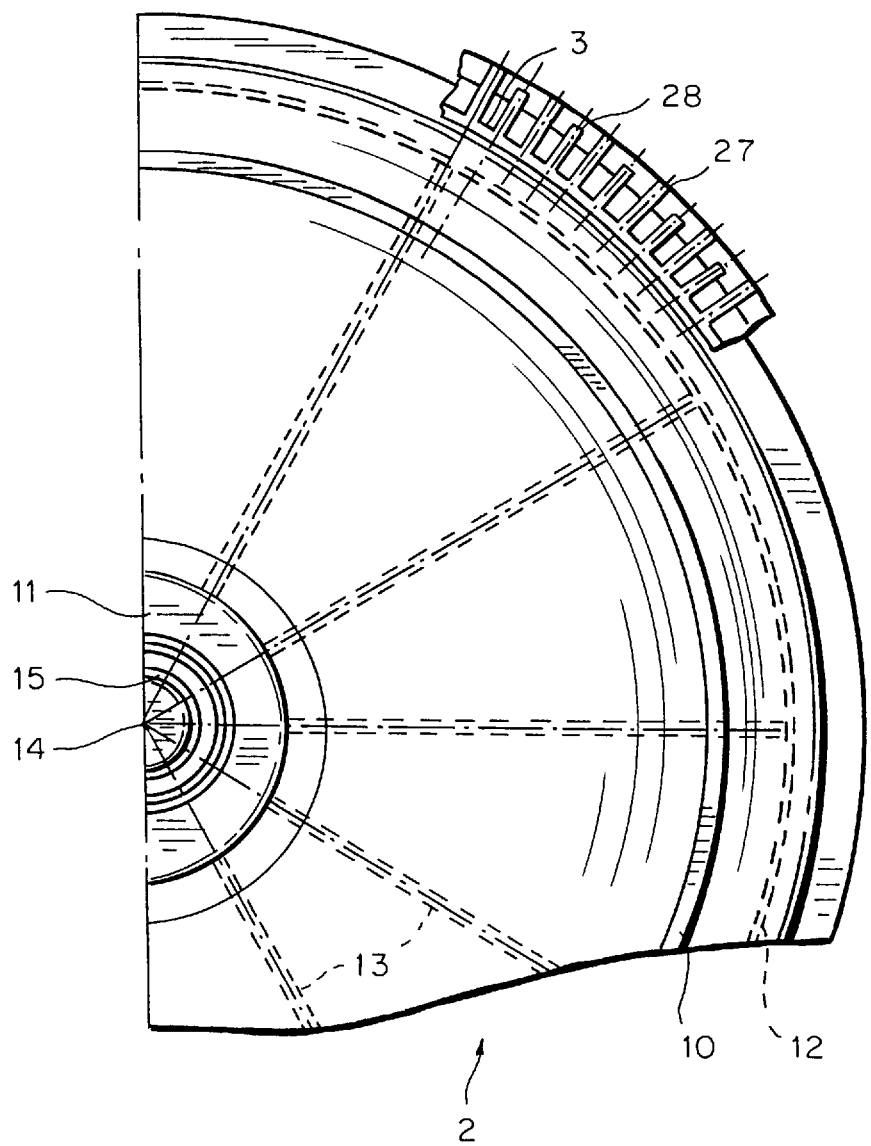
FIG. 3 shows a partial top view of the lid of the container from FIG. 1.

FIG. 2 shows a top view of the receptacle 1; the bottom-stiffening ribs 7 are visible; one of the four brackets 24 is shown with dashed lines. In FIG. 2, the large number of stiffening ribs can be inferred, which support the outer flange of the receptacle 1 in the direction of its side wall 5 and ensure a durable and rigid embodiment. FIG. 3 shows a top view of the lid 2, where a broken away piece of the ring 3 is visible.

Preferably, the cross section of the closure ring 3 should be inferred from FIG. 6. As can be inferred from FIGS. 4 and 6, short stiffening ribs 28 and long stiffening ribs 27 are embodied alternatingly on the outside of the ring 3. By means of this, the ring as a whole is slightly flexible in the radial direction, but is extremely rigid in the axial direction so that the inner groove 23 remains undeformed.

Figure 7:
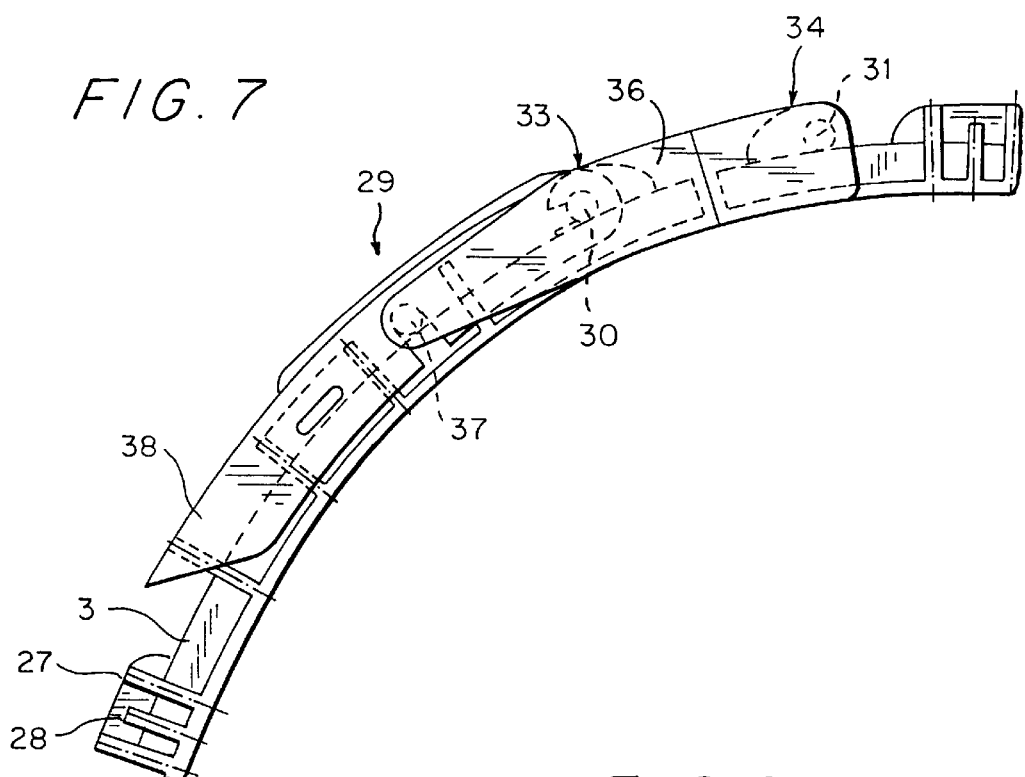
FIG. 7 shows a top view of a turnbuckle of the closure ring.

The turnbuckle can be inferred from FIGS. 4, 5, and 7. The closure ring 3 is radially slotted at one point; two hooks 33, 34 that protrude outward and point away from each other are attached on both sides of this slot. Furthermore, a rib with a longitudinal hole 35 that extends in the circumference direction of the ring is embodied on the side of the slot on which the hook 33 is disposed, spaced apart from this hook.

A clamping lever 38 (FIG. 7) is snapped into the hook 33 with a clamping bolt 30. An elongated tension member 36, which can also be embodied as two superposed flat tension members that enclose the clamping lever 38, is pivotably secured in the tension hook 34 via a securing bolt 31. The other end of the tension member is pivotably attached to the tension lever 38 by means of a coupling bolt 37.

If from the position shown in FIG. 7, the clamping lever is folded out from the ring 3, with its free end in the horizontal direction, then the distance between the securing bolt 31 and the coupling bolt 37 is reduced and the two bolts 30, 31 and therefore also the two hooks 33, 34 are pressed away from each by this procedure. The ring 3 is expanded as a result and can be removed from both outer flanges 16, 17 or can be slid over them. If the clamping lever 38 is pushed back again, then the ring 3 is shortened once more to its fitting size. The possible lengthening of the ring 3 in the circumference direction thereby compensates for attendant tolerances.

In addition, the clamping lever 38 has a bore (not shown in the drawing) which can be brought into alignment with the longitudinal hole 35 so that a clasp, linchpin, or the like can be slid through in order to secure the clamping lever 38 in its closed position.

FIG. 9 shows the clamping lever 38' in a sectional view; this is preferably embodied of a tough plastic that is microwave-permeable. FIG. 5 is the view V in FIG. 4 and shows the top view of the two hooks 33, 34 with the clamping lever 38 removed. In FIG. 9, the clamping lever 38' is shown in a sectional view. All bores and bolts described run parallel to the axis of the ring 3, that is, in the vertical direction with regard to FIG. 1. Please refer to the particular drawings for the precise embodiment of the individual elements.

To ready the sterilization containers for use, the receptacles 1 are stacked one inside the other, as shown in FIG. 1. Here, in each receptacle, the ring 3 is closed over the brackets 24 or 24', as shown in FIG. 9. The turnbuckle 29 of the ring 3 is likewise closed. The ring 3 is consequently secured to the receptacle 1 in captive fashion, but does not interfere with the stacking due to the bottom-stiffening ribs, which are embodied as having a corresponding height. The lids 2 are stored separately, wherein the lid-stiffening ribs 13 of one lid rest upon the upper edge of the outer annular rib 10 of the lid 2 disposed on top of or beneath it.

Now a receptacle is taken from the stack and filled with hospital refuse, for example. After it is full, a lid 2 is taken from the lid stack and inserted into the opening formed by the side wall 5 of the receptacle 1 so that the sealing groove encompasses the upper edge of the side wall 5. The ring 3 is then spread open by using the clamping lever 38, removed from the brackets 24 or 24', and slid over the two outer flanges 16, 17 of the lid 2 and the receptacle 1, respectively. Then the clamping lever 38 is folded back against the outer surface of the ring 3, by means of which the ring is tightened.

As a result, the contents of the receptacle are multiply and hermetically sealed in relation to the environment. Before sterilization, the thin-walled bottom of the flat recess 14 of the lid 2 can be punctured by a hollow needle and the desired quantity of liquid, for example water, can be injected into the interior of the container; it is also possible, though, to pour a particular quantity of fluid into the receptacle before setting the lid 2 on it.

After sealing the puncture point in some known manner, the sterilization container that is filled with moistened refuse is placed in a microwave chamber and exposed to microwave radiation there. As a result of this, the fluid on the inside of the receptacle 1 evaporates, wherein after a time, a pressure/temperature equilibrium sets in. Because of the formation of steam, the container shown is slightly inflated; the stiffening ribs disposed at all danger points assure that both the seal and the integrity of the container are maintained.

The microwaves can penetrate the walls of the container unhindered. After the heating and consequent sterilization of the contents of the container are complete, the container is readied for disposal, wherein a certain vacuum can set in on its inside. In this case too, the stiffening ribs and the embodiment of the sealing device assure that the seal and the container remain sound.

After carrying out the disposal and if need be, after the cleaning of the container, its receptacle and lid can be stored for reuse.

I claim:

1. A reusable sterilization container, preferably for hospital refuse, having a receptacle (1) with a filling opening that is defined by the upper edge of its side wall and is disposed opposite from its bottom, a lid (2) that is for covering the filling opening and is preferably comprised of the same microwave-permeable material as the receptacle (1), and a sealing device with a sealing ring (20) between the receptacle (1) and the lid (2), wherein to guarantee a secure and reliable pressure-tight seal between the receptacle (1) and the lid (2), in addition to the sealing ring (20), which is accommodated in grooves (18, 19) in the receptacle (1) and in the lid (2) that are correspondingly embodied in their cross sectional shape, the sealing device has additional sealing regions (21, 16b; 5b, 22a; 5a, 2a) on the receptacle (1) and the lid (2), and a detachable closure device (3, 29) is provided for securing the lid (2) on the receptacle (1) counter to the force of an internal pressure in the receptacle (1) and can be secured in the closed position if need be, and the receptacle (1)—and if need be, also the lid (2)—is comprised of a tough plastic that resists stretching, even beyond the boiling temperature of water.

2. The container according to claim 1, wherein the side wall (5) of the receptacle (1) tapers all the way from the filling opening to the bottom (4) and can be slid into another receptacle for storage of the receptacles.

3. The container according to claim 1, wherein the inner circumference edge is stiffened by means of a circle of bottom-stiffening ribs (7) between the side wall (5) and bottom (4) of the receptacle (1), whose upper edges form a rest for the outer edge of the bottom (4') of a second receptacle inserted into it.

4. The container according to claim 3, wherein the spacing from the upper edge of the side wall (5) to all of the projections (24, 17) that protrude outward from the outside of the side wall (5) is less than the height of the bottom-stiffening ribs (7).

5. The container according to claim 2, wherein the outer wall (3) is constituted by a series of truncated cone jackets offset from each other and disposed one above the other.

6. The container according to claim 1, wherein the bottom (4) is bowed toward the inside of the receptacle.

7. The container according to claim 6, wherein a central bottom tubular fitting (8) is embodied on the underside of the bottom (4) and does not extend down to the level of the lower edge of the side wall (5) when the receptacle (1) is not acted upon by pressure.

8. The container according to claim 7, wherein a circle of tubular fitting-stiffening ribs (9) is embodied between the outer circumference of the bottom tubular fitting (8) and the underside of the bottom (4).

9. The container according to claim 1, wherein an upward protruding, preferably continuous outer annular rib (10) is embodied on the top side of the lid (2), which is preferably bowed upward; this annular rib is complementary to bottom edge of the receptacle (1) and receives the bottom edge of the receptacle during storage of closed containers.

10. The container according to claim 1 wherein close to the outer circumference of the lid (2), a downward protruding inner annular rib (12) is embodied, which rests fittingly against the inner circumference of the side wall (5) of the receptacle (1).

11. The container according to claim 1 wherein an annular bead (11) that is indented toward the inside of the container is embodied in the center of the lid (2).

12. The container according to claim 10, wherein lid-stiffening ribs (13) are embodied between the annular bead (11) and the inner annular rib (12).

13. The container according to claim 11, wherein the central zone of the non-indented core region of the annular bead (11) is embodied as a flat recess (14) and has a reduced wall thickness in comparison to the other wall thicknesses of the lid (2).

14. The container according to claim 11, wherein an annular groove (15) is disposed in the edge zone of the non-indented core region of the annular bead (11) and is embodied as complementary to the bottom edge of the bottom tubular fitting (8).

15. The container according to claim 1, wherein an outer flange (16, 17) is embodied on or near the upper edge of the receptacle (1), as well as on the outer edge of the lid, and that at least one flexible sealing ring (20) is disposed between the outer flanges (16, 17).

16. The container according to claim 15, wherein an annular groove (18, 19) is embodied in at least one of the outer flanges (16, 17) and constitutes an annular channel for receiving the sealing ring (20).

17. The container according to claim 16, wherein the height of the annular channel (18, 19) is less than the height of the unstressed sealing ring (20), and that the cross sectional surface of the annular channel (18, 19) is at least as great as that of the sealing ring (20).

18. The container according to claim 16, wherein outside the annular channel (18, 19), one of the outer flanges (16, 17), preferably the outer receptacle flange (17), has an annular projection (21) and the other outer flange, preferably the outer lid flange (16), has a recess complementary to the annular projection (21).

19. The container according to claim 15, wherein the closure device for securing the lid (2) to the receptacle (1) is embodied as a device (3, 29) for clamping the two outer flanges (16, 17) together.

20. The container according to claim 19, wherein the downward-pointing surface of the outer receptacle flange (17) and the upward-pointing surface of the outer lid flange (16) converge on each other toward the outside and in particular, have a common cross section in the shape of an equal-leg trapezoid, and that a clamping device with at least one clamping element (3) is provided, which has a complementary cross section and can be slid over the two outer flanges (16, 17) from the outside like a clasp.

21. The container according to claim 20, wherein the slope angles of the downward-pointing surface of the outer receptacle flange (17) and the upward-pointing surface of the outer lid flange (16) each exceed the self-locking angle in relation to the sliding direction, of the at least one clamping element (3), preferably in relation to the horizontal direction.

22. The container according to claim 21, wherein the clamping element is embodied as an annular body (3) that encompasses both outer flanges (16, 17) from the outside.

23. The container according to claim 22, wherein the annular body is embodied as a preferably one-piece, resilient ring (3) made of plastic, preferably of the same plastic of which the receptacle (1) and/or the lid (2) is comprised, that the ring (3) has an inner groove (23) pointing toward the center, whose cross section corresponds to that of the two outer flanges (16, 17), that the ring (3) has a radial slot in at least one place, and that the radial slot is bridged by a clamping device (29).

24. The container according to claim 23, wherein the clamping device (29) has a clamping lever (38), which is supported with its one end on the ring (3) next to the one side of the radial slot so it can pivot around a pivot axis parallel to the ring axis, and which is connected to a point of the ring (3) on the other side of the radial slot via a tension member (36) that is articulatingly coupled to both sides.

25. The container according to claim 24, wherein the ring (3) has an essentially Y-shaped cross section, wherein the inner flanks of the two arms of the Y define the inner groove (23), and that ring-stiffening ribs (27, 28) are embodied between the outer flanks of both arms of the Y and the corresponding side of the longitudinal bar of the Y, respectively.

26. The container according to claim 25, wherein the short annular stiffening ribs (28) and the long annular stiffening ribs (27) extend alternatingly to the center or to the longitudinal bar of the Y.

27. The container according to claim 15, wherein flange-stiffening ribs are embodied between the part of the lower surface of the outer receptacle flange (17), which engages with the closure device (3), and the adjoining part of the outer surface of the side wall (5) of the receptacle (1).

28. The container according to claim 23, wherein an annular support (24) is embodied on the outside of the side wall (5) of the receptacle (1), below the outer receptacle flange (17), and is for storing the ring (3) when the lid (2) is removed.

29. The container according to claim 28, wherein the annular support is preferably embodied by four brackets (24) distributed around the outer circumference of the side wall (5).

30. The container according to claim 29, wherein the outer circumference described by the brackets (24) is smaller than the outer diameter of the outer flanges (16, 17) and is greater than the inner diameter of the ring (3) when the clamping device (29) is closed, so that the closed ring (3) can loosely, but non-detachably enclose the outer edges of the brackets (24).

31. The container according to claim 29, wherein bracket-stiffening ribs (25) are embodied between the undersides of the brackets (24) and the adjoining outer surface of the side wall (5) of the receptacle (1).

32. The container according to claim 31, wherein the brackets pass through the flange-stiffening ribs and that separate longitudinal ribs (26) are embodied between the upper edge of these brackets and the underside of the outer receptacle flange (17).

33. The container according to claim 29, wherein the brackets (24) are embodied as handles, preferably because of their disposition sloped slightly downward and outward.

34. The container according to claim 10, wherein the side wall (5) of the receptacle (1) is elongated upward beyond the outer receptacle flange (17) and that the lid (2) has a sealing groove that opens toward the bottom, between the inner annular rib (12) and its outer lid wall (22) that extends to the outer lid flange (16) and encompasses the upper edge of the receptacle (1); the upper edge of the side wall (5) of the receptacle (1) extends into this sealing groove.

35. The container according to claim 34, wherein the groove bottom of the sealing groove tapers toward the top and ends in a hollow, that the upper edge of the side wall (5) of the receptacle (1) has a rounded part, which rests on the hollow, and that the radius of the rounded part is smaller than that of the hollow.

36. The container according to claim 35, wherein a circumference gap is formed between the outer lid wall (22)

and the outer surface region of this side wall (5) that adjoins the upper edge of the side wall (5) of the receptacle (1), which gap permits the side wall (5) to bulge because of internal pressure without damaging the outer lid wall (22).

37. The container according to claim 15, wherein the outer surface of the side wall (5) of the receptacle (1) tapers conically in the region extending upward from the outer receptacle flange (17), and that the inner surface region of the outer lid wall (22) adjoining the outer lid flange (16) is embodied as complementary to the outer receptacle flange in order to form a sealing conical seat.

38. The container according to claim 1, wherein the receptacle (1) and/or the lid (2) and/or the ring (3) is embodied as a one-piece injection-molded part.

39. The container according to claim 1, wherein the receptacle (1) has at least one subdivision for receiving preselected refuse.

* * * * *